United States Patent
Yamada et al.

(10) Patent No.: US 10,794,723 B2
(45) Date of Patent: Oct. 6, 2020

(54) WALKING MEASUREMENT DEVICE, WALKING MEASUREMENT METHOD, AND PROGRAM

(71) Applicants: ALPS ALPINE CO., LTD., Tokyo (JP); JINS HOLDINGS Inc., Gunma (JP)

(72) Inventors: Yukimitsu Yamada, Miyagi (JP); Susumu Nakamura, Saitama (JP); Shunsuke Shioya, Kanagawa (JP)

(73) Assignees: ALPS ALPINE CO., LTD., Tokyo (JP); JINS HOLDINGS Inc., Gunma (JP)

( * ) Notice: Subject to any disclaimer, the term of this patent is extended or adjusted under 35 U.S.C. 154(b) by 325 days.

(21) Appl. No.: 15/935,474

(22) Filed: Mar. 26, 2018

(65) Prior Publication Data
US 2018/0209814 A1    Jul. 26, 2018

Related U.S. Application Data

(63) Continuation of application No. PCT/JP2016/079539, filed on Oct. 4, 2016.

(30) Foreign Application Priority Data

Oct. 13, 2015  (JP) .................. 2015-202485

(51) Int. Cl.
 *G01C 22/00*  (2006.01)
 *A61B 5/11*  (2006.01)
 *G06M 3/00*  (2006.01)

(52) U.S. Cl.
 CPC .............. *G01C 22/006* (2013.01); *A61B 5/11* (2013.01); *A61B 5/112* (2013.01); *G06M 3/00* (2013.01)

(58) Field of Classification Search
 CPC .......... G01C 22/006; A61B 5/11; A61B 5/112; G06M 3/00
 See application file for complete search history.

(56) References Cited

U.S. PATENT DOCUMENTS 8,460,001 B1 * 6/2013 Chuang .............. G09B 19/0038
434/247
2009/0030350 A1   1/2009 Yang et al.
(Continued)

FOREIGN PATENT DOCUMENTS

JP    2002-221434    8/2002
JP    2009-106387    5/2009
(Continued)

OTHER PUBLICATIONS

Extended European Search Report for 16855315.4 dated Oct. 18, 2018.
(Continued)

*Primary Examiner* — Mohammad K Islam
(74) *Attorney, Agent, or Firm* — IPUSA, PLLC

(57) ABSTRACT

A walking measurement device is provided that includes a timing detection unit configured to detect an impact generation timing at which an impact resulting from a landing of a left foot or a right foot has been generated; an acceleration sensor configured to repeatedly detect, at predetermined time intervals, an acceleration in a lateral direction along which the left foot and the right foot are arranged side by side; and a first determination unit configured to determine whether the impact generation timing corresponds to a landing timing of the left foot or a landing timing of the right foot based on the impact generation timing detected by the timing detection unit and the acceleration detected by the acceleration sensor.

19 Claims, 12 Drawing Sheets

(56) References Cited

U.S. PATENT DOCUMENTS

| | | | |
|---|---|---|---|
| 2009/0240171 A1* | 9/2009 | Morris Bamberg | A61B 5/1038 600/595 |
| 2011/0152727 A1* | 6/2011 | Ten Kate | G08B 21/0446 600/595 |
| 2012/0101763 A1 | 4/2012 | Sambongi | |
| 2013/0123669 A1 | 5/2013 | Kinoshita et al. | |
| 2013/0178958 A1* | 7/2013 | Kulach | A61B 5/6807 700/91 |
| 2013/0178983 A1* | 7/2013 | Watabe | G05D 1/0251 700/258 |
| 2015/0081061 A1* | 3/2015 | Aibara | A61B 5/1122 700/91 |
| 2015/0081245 A1* | 3/2015 | Nagasaka | G01P 3/64 702/141 |
| 2015/0088408 A1 | 3/2015 | Yamaoka | |
| 2015/0185043 A1* | 7/2015 | Jain | A43B 3/001 702/160 |
| 2016/0045140 A1* | 2/2016 | Kitamura | A61B 5/1128 600/595 |
| 2016/0066820 A1* | 3/2016 | Sales | G08B 21/0476 600/595 |
| 2017/0344919 A1* | 11/2017 | Chang | A61B 5/1118 |
| 2018/0325467 A1* | 11/2018 | Matsumura | A61B 5/0077 |
| 2018/0358119 A1* | 12/2018 | Bhushan | G06F 1/163 |

FOREIGN PATENT DOCUMENTS

| | | |
|---|---|---|
| JP | 2009-525107 | 7/2009 |
| JP | 2012-024449 | 2/2012 |
| JP | 2012-088253 | 5/2012 |
| JP | 2013-190377 | 9/2013 |
| JP | 2015-087377 | 5/2015 |
| WO | 2013/105039 | 7/2013 |
| WO | 2014/181601 | 11/2014 |

OTHER PUBLICATIONS

International Search Report dated Dec. 27, 2016 in PCT/JP2016/079539 filed on Oct. 4, 2016.
Japanese Office Action for 2017-545166 dated Mar. 26, 2019.

* cited by examiner

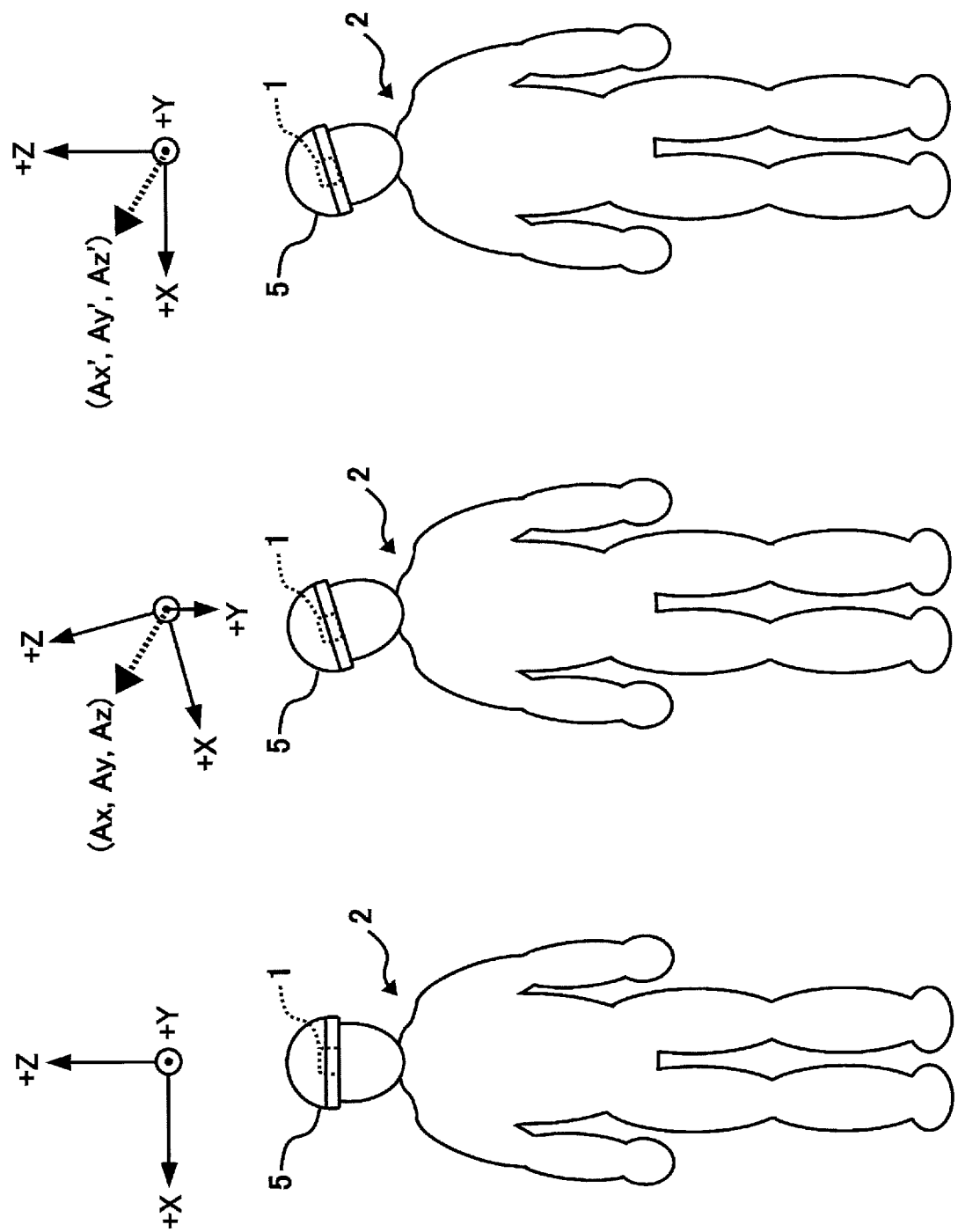

WALKING MEASUREMENT DEVICE, WALKING MEASUREMENT METHOD, AND PROGRAM

CROSS-REFERENCE TO RELATED APPLICATIONS

The present application is a continuation application filed under 35 U.S.C. 111(a) claiming benefit under 35 U.S.C. 120 and 365(c) of PCT International Application No. PCT/JP2016/079539 filed on Oct. 4, 2016 and designating the U.S., which claims priority to Japanese Patent Application No. 2015-202485 filed on Oct. 13, 2015. The entire contents of the foregoing applications are incorporated herein by reference.

BACKGROUND OF THE INVENTION

1. Field of the Invention

The present invention relates to a walking measurement device that uses an acceleration sensor to make measurements associated with walking.

2. Description of the Related Art

Pedometers that count the number of steps taken by a user by detecting the motion of a movable body part associated with walking are known. For example, Japanese Unexamined Patent Application Publication No. 2002-221434 describes a wrist watch type pedometer that uses an electrical contact to detect a pendulum motion associated with walking.

In making measurements associated with a walking motion, information other than the number of steps are also desired, such as whether each step of a walking motion is made by the right foot or the left foot landing on the ground. However, pedometers are typically incapable of obtaining such information.

In the pedometer described in Japanese Unexamined Patent Application Publication No. 2002-221434, an impact acceleration resulting from the foot coming into contact with the ground causes a pendulum to come into contact with a contact portion, and the contact portion is turned on/off each time such contact is made. In this way, the number of steps can be obtained by counting the number of times the contact portion has been turned on/off. However, the acceleration acting on the pendulum is not limited to the impact acceleration resulting from the foot coming contact with the ground but may also include an acceleration caused by the movement of an arm that is unrelated to walking, for example. Thus, in the above-described method of only detecting the acceleration of the pendulum, a pendulum motion that is unrelated to the foot landing on the ground may be erroneously counted as a step, and as a result, accuracy of the step count may be compromised.

SUMMARY OF THE INVENTION

Aspects of the present invention are directed to providing a walking measurement device and a walking measurement method that can determine whether each step of a walking motion is made by the landing of the right foot or the left foot.

According to one aspect of the present invention, a walking measurement device is provided that includes a timing detection unit configured to detect an impact generation timing at which an impact resulting from a landing of a left foot or a right foot has been generated; an acceleration sensor configured to repeatedly detect, at predetermined time intervals, an acceleration in a lateral direction along which the left foot and the right foot are arranged side by side; and a first determination unit configured to determine whether the impact generation timing corresponds to a landing timing of the left foot or a landing timing of the right foot based on the impact generation timing detected by the timing detection unit and the acceleration detected by the acceleration sensor.

According to another aspect of the present invention, a walking measurement method is provided that is implemented by a computer to measure a walking motion based on a detection result of an acceleration sensor that detects an acceleration in a lateral direction along which a left foot and a right foot are arranged side by side. The walking measurement method includes steps of detecting an impact generation timing at which an impact resulting from a landing of the left foot or the right foot has been generated; controlling the acceleration sensor to repeatedly detect the acceleration in the lateral direction at predetermined time intervals; and determining, based on the detected impact generation timing and the detected acceleration, whether the impact generation timing corresponds to a landing timing of the left foot or a landing timing of the right foot.

BRIEF DESCRIPTION OF THE DRAWINGS

FIGS. 12A-12C are diagrams illustrating an acceleration conversion process according to a posture change.

DESCRIPTION OF THE EMBODIMENTS

First Embodiment

In the following; a walking measurement device according to a first embodiment of the present invention will be described with reference to the accompanying drawings.

Figure 1:
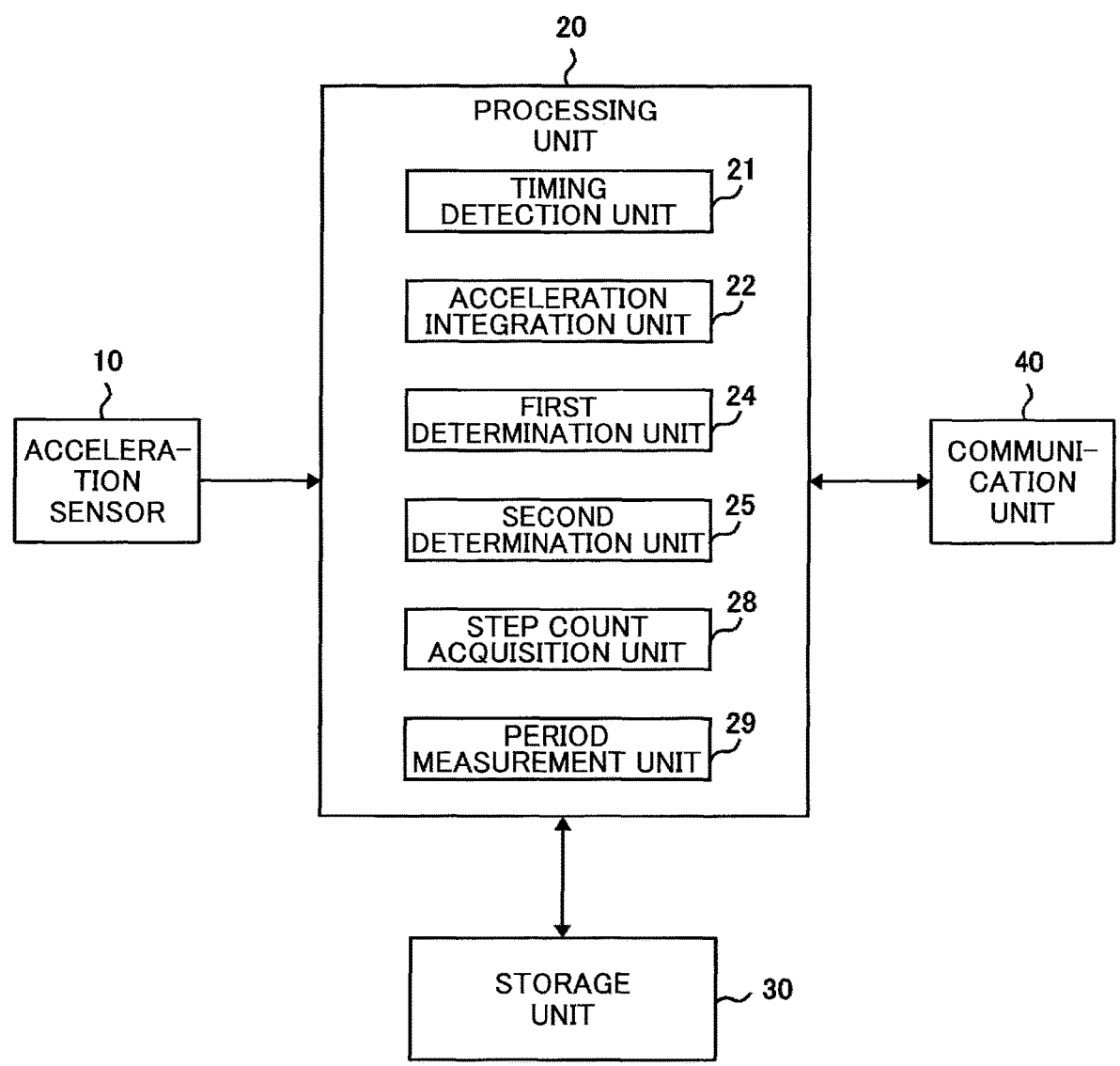
FIG. 1 is a diagram showing an example configuration of a walking measurement device according to a first embodiment of the present invention.
Figure 2:
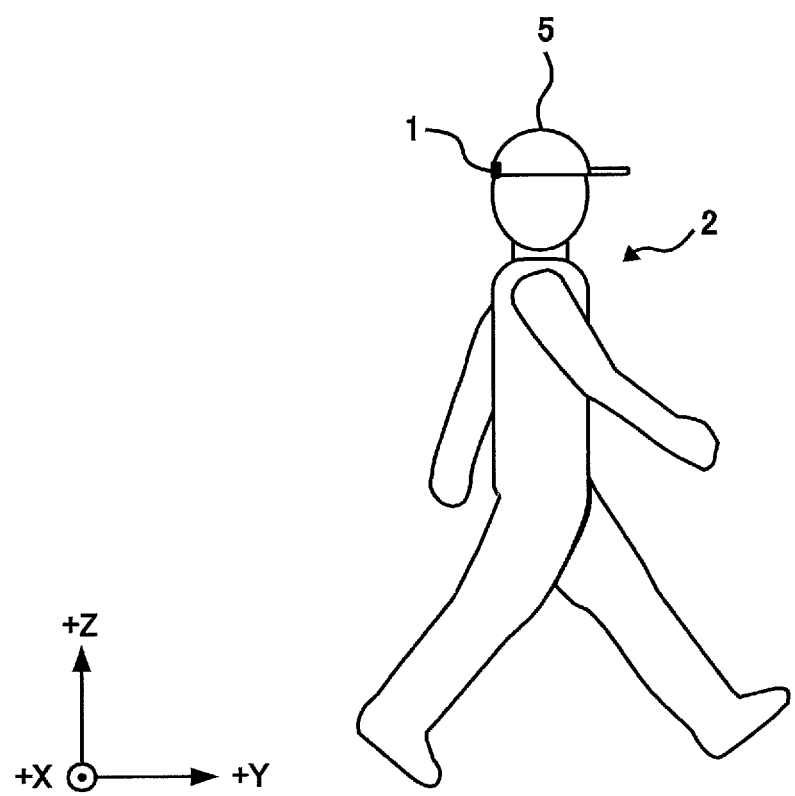
FIG. 2 is a diagram showing an example method of mounting the walking measurement device.
Figure 3:
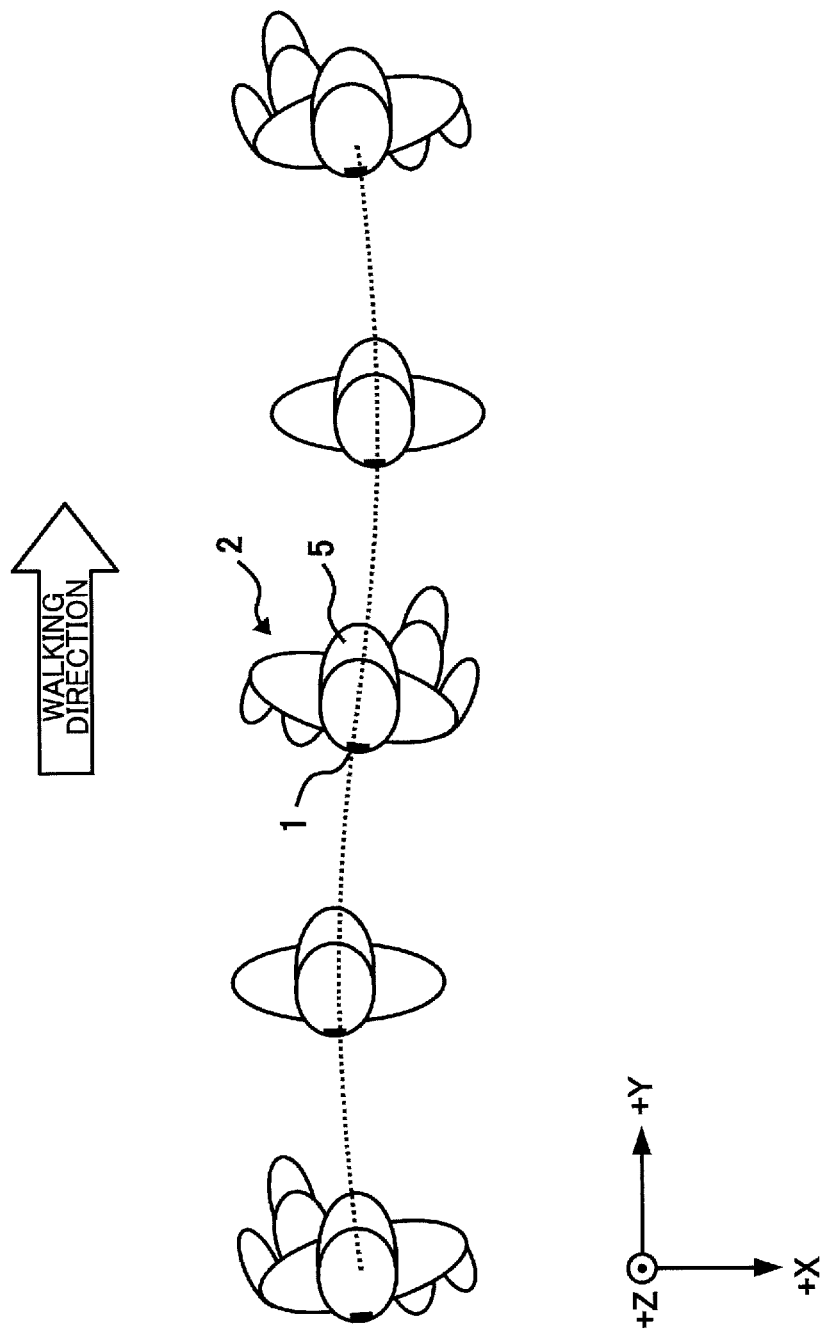
FIG. 3 is a diagram illustrating lateral movements of a body in a walking motion.

FIG. 1 is a diagram showing an example configuration of a walking measurement device 1 according to the present embodiment. FIG. 2 is a diagram showing an example method of mounting the walking measuring apparatus 1. FIG. 3 is a diagram illustrating lateral movements of the body in a walking motion. Note that in FIGS. 2 and 3, the Z-axis represents the vertical direction perpendicular to the ground, the X-axis represents the lateral direction along which the left foot and right foot are arranged side by side in the body, and the Y-axis represents the anterior-posterior direction of the body perpendicular to the Z-axis and the X-axis.

The walking measurement device 1 according to the present embodiment determines whether the left foot or the right foot has landed in a walking motion and determines the period of one step of the walking motion based on an acceleration of the walking motion; more specifically, an acceleration of the walking motion in the lateral direction (X-axis direction in FIGS. 2 and 3) along which the left foot and the right foot are arranged side by side. As such, the walking measurement device 1 is preferably mounted at a position that is sensitive to changes in the lateral acceleration of the walking motion. In the example of FIG. 2, the walking measurement device 1 is attached to a rear side portion of a cap 5 worn by a pedestrian 2. Note that the mounting position of the walking measurement device 1 is not limited to the example of FIG. 2. In other examples, the walking measurement device 1 may be attached to a top portion or a brim portion of the cap 5, for example. Also, the walking measurement device 1 is not limited to being attached to a cap but may also be mounted to a hands-free device, a headset, a hearing aid, or glasses, for example.

As shown in FIG. 3, in a normal walking motion, the center of the body of the pedestrian 2 swings to the left/right with each step. During the period from when the left foot lands until the right foot lands (left foot landing period), the moving direction of the body is reversed from left to right, and as such, an acceleration to the right (rightward acceleration) becomes the dominant lateral acceleration. On the other hand, during the period from when the right foot lands until the left foot lands (right foot landing period), the moving direction of the body is reversed from right to left, and as such, an acceleration to the left (leftward acceleration) becomes the dominant lateral acceleration. The walking measurement device 1 according to the present embodiment relies on the difference in the lateral acceleration during the left foot landing period and the right foot landing period to determine whether a landing foot corresponds to the left foot or the right foot and determine the period of one step.

The walking measurement device 1 shown in FIG. 1 includes an acceleration sensor 10, a processing unit 20, a storage unit 30, and a communication unit 40.

The acceleration sensor 10 detects an acceleration in the lateral direction (X-axis direction in FIGS. 2 and 3) along which the left foot and right foot are arranged side by side in the body, an acceleration in the vertical direction (Z-axis direction in FIGS. 2 and 3) perpendicular to the ground, and an acceleration in the anterior-posterior direction (Y-axis direction in FIGS. 2 and 3) perpendicular to the lateral direction and the vertical direction. For example, the acceleration sensor 10 may be configured to include a MEMS (micro electro mechanical systems) based triaxial acceleration sensor. The acceleration sensor 10 repeatedly detects the accelerations in the three directions at predetermined time intervals under the control of the processing unit 20.

The communication unit 40 is a device for exchanging data with an external device (not shown) using a predetermined communication method. For example, the communication unit 40 may receive from an external device, a command for causing the processing unit 20 to execute a predetermined process and data to be used for executing the process. Also, the communication unit 40 may transmit to an external device, data representing processing results of the processing unit 20 (e.g., data on the number of steps, data on the period of one step of a walking motion). For example, the communication unit 40 may include a communication module, such as a Bluetooth (registered trademark) module, that establishes relatively short distance communication with a portable device, such as a smartphone.

The processing unit 20 is a device that controls overall operations of the walking measurement device 1. The processing unit 20 may be configured to include a computer that executes a process according to a program loaded in the storage unit 30, for example. The program may be stored in a ROM and loaded in the storage unit 30, or the program may be downloaded from an external device via the communication unit 40, for example. Also, the program may be input from an external source via an interface device, such as a USB, or a recording medium reading device, and written in the storage unit 30, for example. Note that in some embodiments, all process operations of the processing unit 20 may be executed by a computer, and in other embodiments, at least a part of the process operations of the processing unit 20 may be executed by a dedicated hardware circuit, for example.

The processing unit 20 includes a timing detection unit 21, an acceleration integration unit 22, a first determination unit 24, a second determination unit 25, a step count acquisition unit 28, and a period measurement unit 29 as process units related to walking measurement.

The timing detection unit 21 detects the timing of the impact generated from the left foot or right foot landing on the ground, based on the accelerations in the plurality of directions (X-axis direction, Y-axis direction, Z-axis direction) detected by the acceleration sensor 10. That is, the timing detection unit 21 calculates an evaluation value E indicating the magnitude of the impact of a foot landing based on the accelerations in the plurality of directions detected by the acceleration sensor 10 and detects, as the impact generation timing, the timing at which a peak of the evaluation value E exceeding a predetermined threshold value Eth has occurred. The evaluation value E may be represented by the following formula (1), for example.

$$E = \sqrt{(Ax^2 + Ay^2 + Az^2)} \qquad (1)$$

In the above formula (1), "Ax" represents the acceleration in the lateral direction (X-axis direction), "Ay" represents the acceleration in the anterior-posterior direction (Y-axis direction), "Az" represents the acceleration in the vertical direction (Z-axis direction). The timing detection unit 21 calculates an evaluation value E each time the acceleration sensor 10 detects the accelerations in above directions and detects the timing at which a peak of the evaluation value E exceeding the threshold value Eth has occurred.

The acceleration integration unit 22 obtains an integrated value S of the acceleration Ax in the lateral direction (X-axis direction) detected by the acceleration sensor 10 over an intermediate period (interval) between two consecutive impact generation timings (foot landing timings) that have been consecutively detected by the timing detection unit 21. For example, each time the timing detection unit 21 detects the impact generation timing of an impact generated from a foot landing, the acceleration integration unit 22 may obtain an integrated value S of the acceleration Ax over the intermediate period between the most recent impact generation timing and a previous impact generation timing.

The first determination unit 24 determines whether the impact generation timing detected by the timing detection unit 21 corresponds to the landing timing of the left foot or the landing timing of the right foot based on the impact generation timing detected by the timing detection unit 21 and the lateral acceleration Ax detected by the acceleration sensor 10.

For example, the first determination unit 24 may compare two integrated values S obtained with respect to two consecutive intermediate periods that are temporally separated by one impact generation timing, and based on the comparison, the first determination unit 24 may determine whether the one impact generation timing corresponds to the landing timing of the left foot or the landing timing of the right foot.

In the following descriptions, impact generation timings detected by the timing detection unit 21 are each assigned a sequential number "n" (where n=1, 2, 3, ... ), and the impact generation timing with the sequential number "n" is denoted as "t(n)". Also, an intermediate period (interval) between two consecutive impact generation timings t(n) and t(n+1) is denoted as "T(n)", and an integrated value of the acceleration Ax over the intermediate period T(n) is denoted as "S(n)". In this case, the first determination unit 24 compares the two integrated values S(n−1) and S(n) obtained with respect to the two consecutive intermediate periods T(n−1) and T(n), and determines whether the impact generation timing t(n) temporally separating the two consecutive intermediate periods T(n−1) and T(n) corresponds to the landing timing of the left foot or the landing timing of the right foot.

For example, it is assumed below that the acceleration sensor 10 detects a positive acceleration Ax when the direction of the acceleration Ax is rightward ("+X" direction in FIGS. 2 and 3), and the acceleration sensor 10 detects a negative acceleration Ax when the direction of the acceleration Ax is leftward (the direction opposite the "+X" direction in FIGS. 2 and 3). In this case, the integrated value S of the acceleration Ax during the "left foot landing period" in which the rightward acceleration is dominant is greater than the integrated value S of the acceleration Ax during the "right foot landing period" in which the leftward acceleration is dominant. Accordingly, when the integrated value S(n) is greater than the integrated value S(n−1), the first determination unit 24 determines that the impact generation timing t(n) corresponds to the landing timing of the left foot, and when the integrated value S(n) is less than the integrated value S(n−1), the first determination unit 24 determines that the impact generation timing t(n) corresponds to the landing timing of the right foot.

Each time the acceleration integration unit 22 obtains an integrated value S(n), the first determination unit 24 compares the integrated value S(n) for the most recent intermediate period T(n) with the integrated value S(n−1) for the previous intermediate period T(n−1), and obtains a comparison determination value indicating the determination result of the comparison. In the following descriptions, the most recently obtained comparison determination value is denoted as "F", and a previously obtained comparison determination value is denoted as "F_old". Also, note that the comparison determination value F is set to "0" in the case where S(n−1)<S(n), and the comparison determination value F is set to "1" in the case where S(n−1)>S(n). In this case, the value "0" as the comparison determination value F indicates that the impact generation timing corresponds to the landing timing of the left foot, and the value "1" as the comparison determination value F indicates that the impact generation timing corresponds to the landing timing of the right foot.

The second determination unit 25 determines whether an intermediate period between two consecutive impact generation timings corresponds to the period of one step of a walking motion. That is, when the comparison determination results obtained by the first determination unit 24 with respect to two consecutive impact generation timings t(n−1) and t(n) are different (e.g., when F_old≠F), the second determination unit 25 determines that one intermediate period (e.g., intermediate period T(n−1)), from among three consecutive intermediate periods T(n−2), T(n−1), and T(n) that are temporally separated by the two impact generation timings t(n−1) and t(n), corresponds to the period of one step of the walking motion.

For example, when the most recent comparison determination value F obtained by the first determination unit 24 is different from the previous comparison determination value F_old, the second determination unit 25 determines that one intermediate period (e.g., intermediate period T(n−1)), from among the three consecutive intermediate periods T(n−2), T(n−1), and T(n) that are temporally separated by the two impact generation timings t(n−1) and t(n) associated with the above comparison determination values F and F_old, corresponds to the period of one step of the walking motion.

The step count acquisition unit 28 counts the number of times the second determination unit 25 has determined that a given intermediate period corresponds to the period of one step of the walking motion, and acquires the counted number as the number of steps. The step count acquisition unit 28 stores the acquired data relating to the number of steps in the storage unit 30.

The period measurement unit 29 measures the duration of the intermediate period that has been determined to correspond to the period of one step of the walking motion by the second determining unit 25. For example, the period measurement unit 29 may acquire data relating to the duration of the intermediate period, such as the number of detections made by the acceleration sensor 10 that repeatedly detects the acceleration at predetermined time intervals. The period measurement unit 29 stores the data relating to the duration of the intermediate period in the storage unit 30 together with the result of the left/right foot landing determination made by the first determination unit 24.

The storage unit 30 stores computer programs to be executed by the processing unit 20, constant data used by the processing unit 20 in executing process operations, variable data temporarily held during execution of a process, and processing result data (e.g., number of steps, duration of intermediate period, left/right foot landing determination), for example. The storage unit 30 may include a ROM, a RAM, and a nonvolatile memory, for example.

In the following, process operations of the walking measurement device 1 according to the present embodiment having the above-described configuration will be described.

Figure 4:
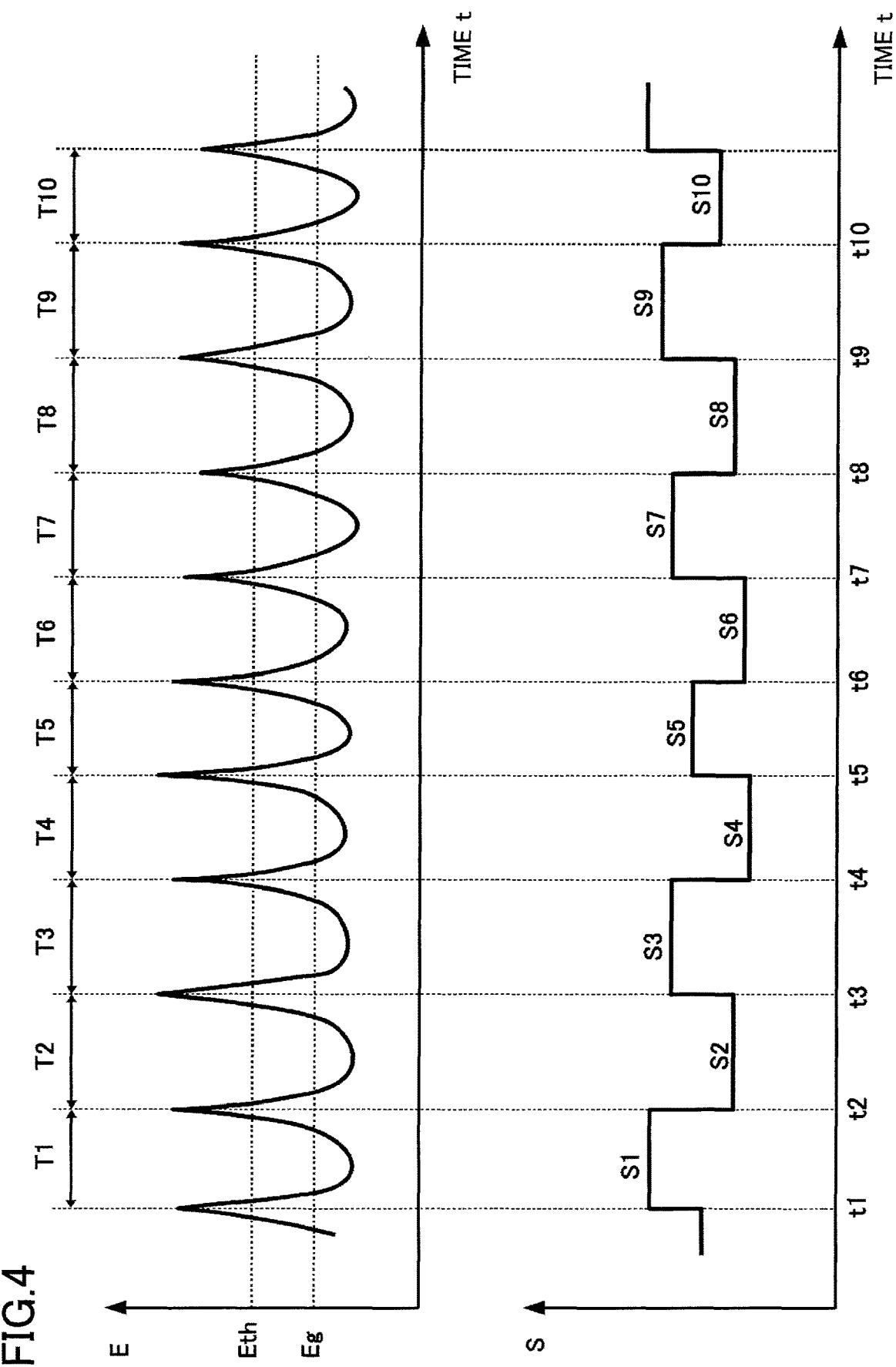
FIG. 4 is a first graph representing temporal changes in an evaluation value indicating the magnitude of an impact of a foot landing and an integrated value of an acceleration in the lateral direction.
Figure 5:
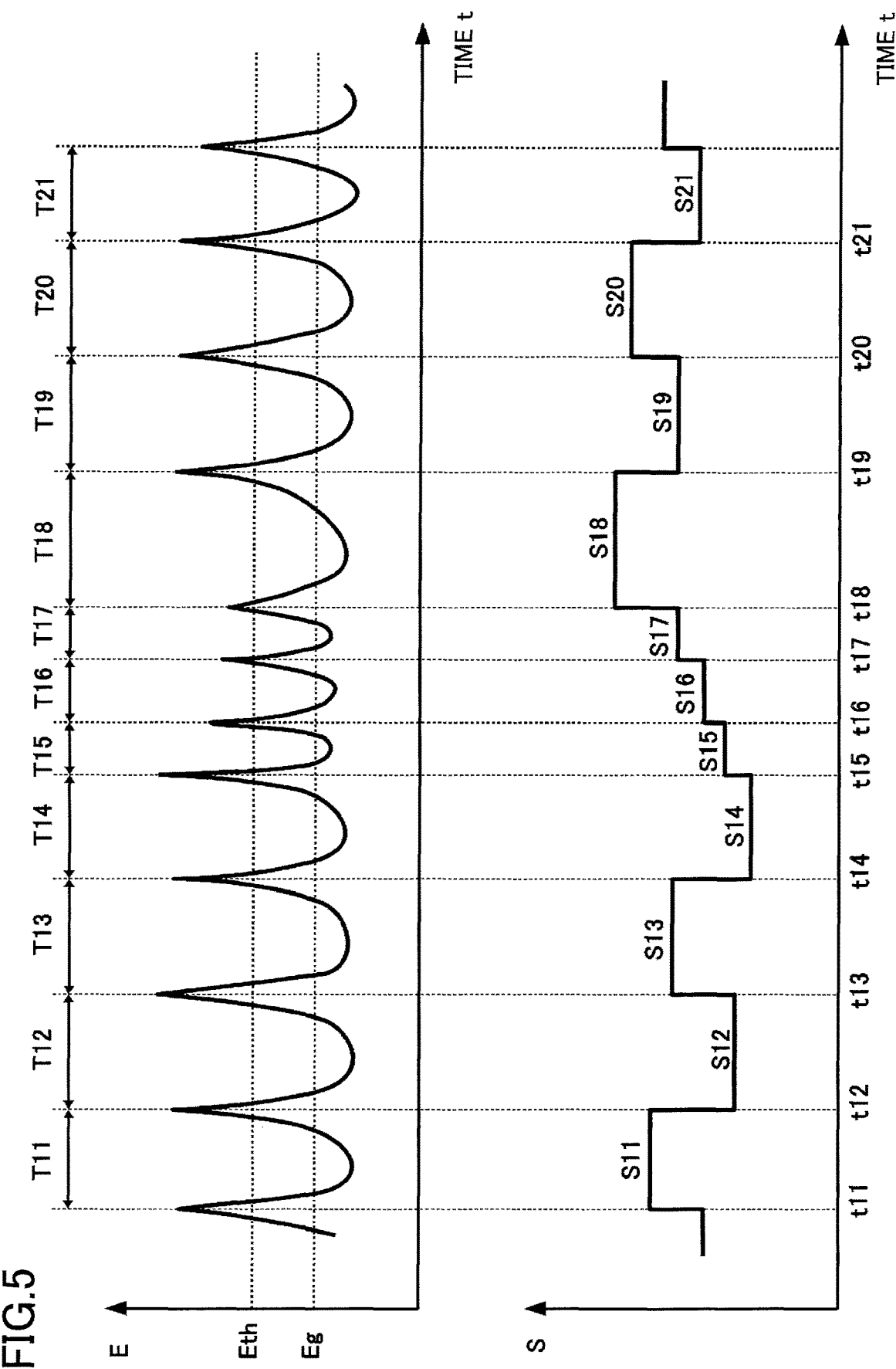
FIG. 5 is a second graph representing temporal changes in the evaluation value indicating the magnitude of the impact of a foot landing and the integrated value of the acceleration in the lateral direction.

FIGS. 4 and 5 are graphs showing temporal changes in the evaluation value E indicating the magnitude of the impact generated from a foot landing and the integrated value S of the lateral acceleration Ax. In these graphs, "t1" to "t21" represent impact generation timings detected by the timing detection unit 21, and "T1" to "T21" represent intermediate periods with respect to which an integrated value S is calculated by the acceleration integration unit 22.

As shown in FIGS. 4 and 5, when a foot lands on the ground, a peak occurs in the evaluation values E calculated by the timing detection unit 21. The timing detection unit 21 detects a peak occurring in the evaluation values E that exceeds the threshold value Eth as an impact generation timing. Note that in FIGS. 4 and 5, "Eg" represents the evaluation value E in a resting state, i.e., a value corresponding to the acceleration due to gravity. For example, the timing detection unit 21 may obtain the value for "Eg" by calculating the average value of the evaluation values E obtained in a resting state, and the timing detection unit 21 may add a predetermined offset value to "Eg" to obtain the threshold value Eth.

As shown in FIG. 4, the integrated value S in a normal walking motion changes by alternately increasing and decreasing in a regular pattern. Such change results from the alternate repetition of the right foot landing period in which the leftward acceleration Ax is dominant and the left foot landing period in which the rightward acceleration Ax is dominant. In the example illustrated in FIG. 4, the integrated value S obtained with respect to the left foot landing period is greater than the integrated value S obtained with respect to the right foot landing period. For example, in FIG. 4, the change from the integrated value S1 to the integrated value S2 (S1>S2) represents a transition from the left foot landing period to the right foot landing period, and as such, the first determination unit 24 determines that the impact generation timing t2 corresponds to the landing timing of the right foot. Also, in FIG. 4, the change from the integrated value S2 to the integrated value S3 (S2<S3) represents a transition from the right foot landing period to the left foot landing period, and as such, the first determination unit 24 determines that the impact generation timing t3 corresponds to the landing timing of the left foot. Further, because the determination results obtained by the first determination unit 24 with respect to the two consecutive impact generation timings t2 and t3 differ from one another, the second determination unit 25 determines that the intermediate period T2 between the impact generation timings t2 and t3 corresponds to the period of one step of the walking motion.

On the other hand, in FIG. 5, the integrated values S14 to S18 increase monotonously, thereby deviating from the regular increase/decrease pattern of change in the integrated value S. That is, during the intermediate periods T15, T16, and T17, each of the two consecutive impact generation timings defining each of these intermediate periods (i.e., t15 and t16, t16 and t17, t17 and t18) correspond to the landing timing of the left foot. As such, with respect to the intermediate periods T15, T16, and T17, the second determination unit 25 determines that these intermediate periods do not correspond to the period of one step of the walking motion.

Figure 6:
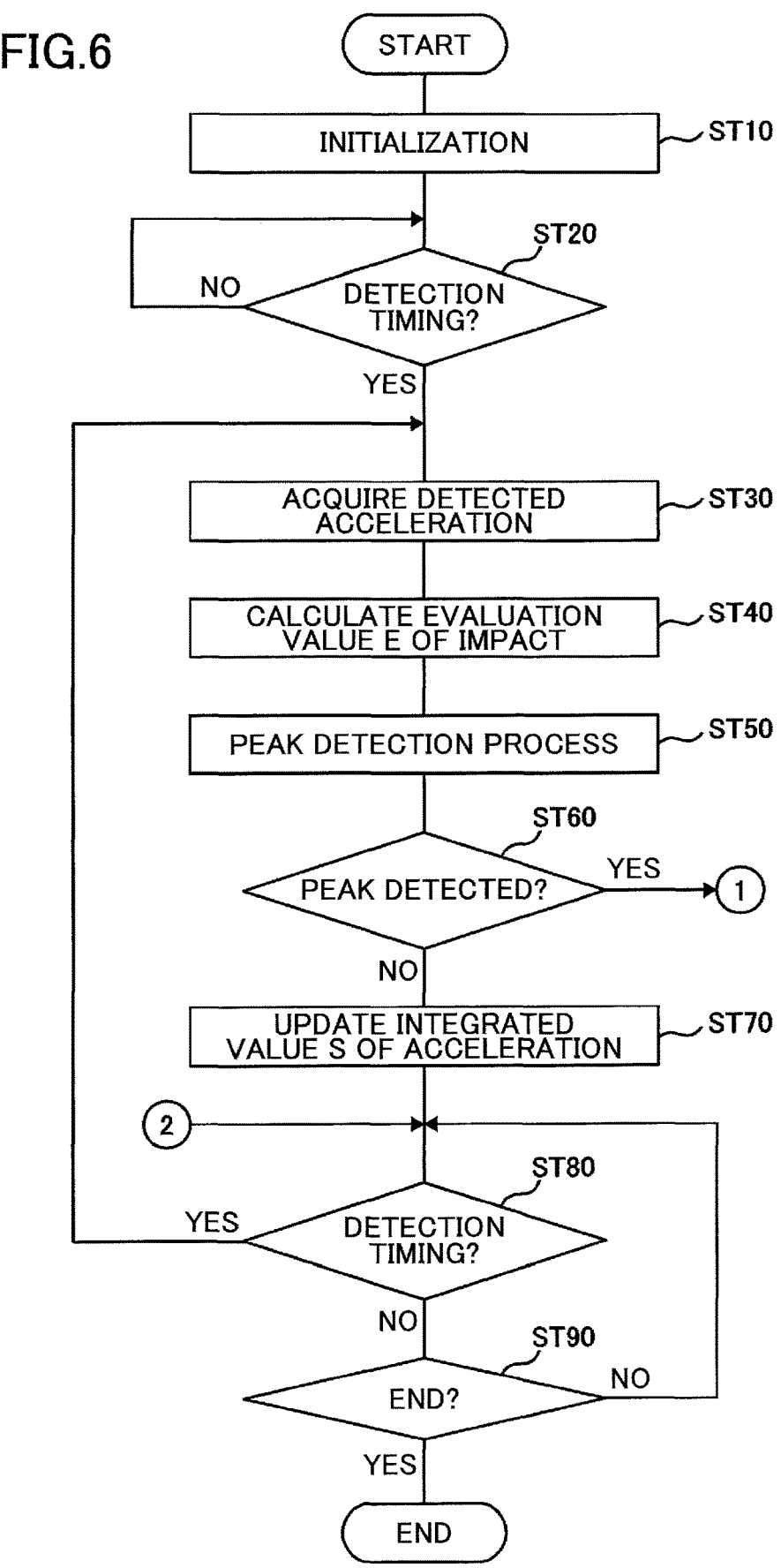
FIG. 6 is a first flowchart illustrating operations of the walking measurement device according to the first embodiment.
Figure 7:
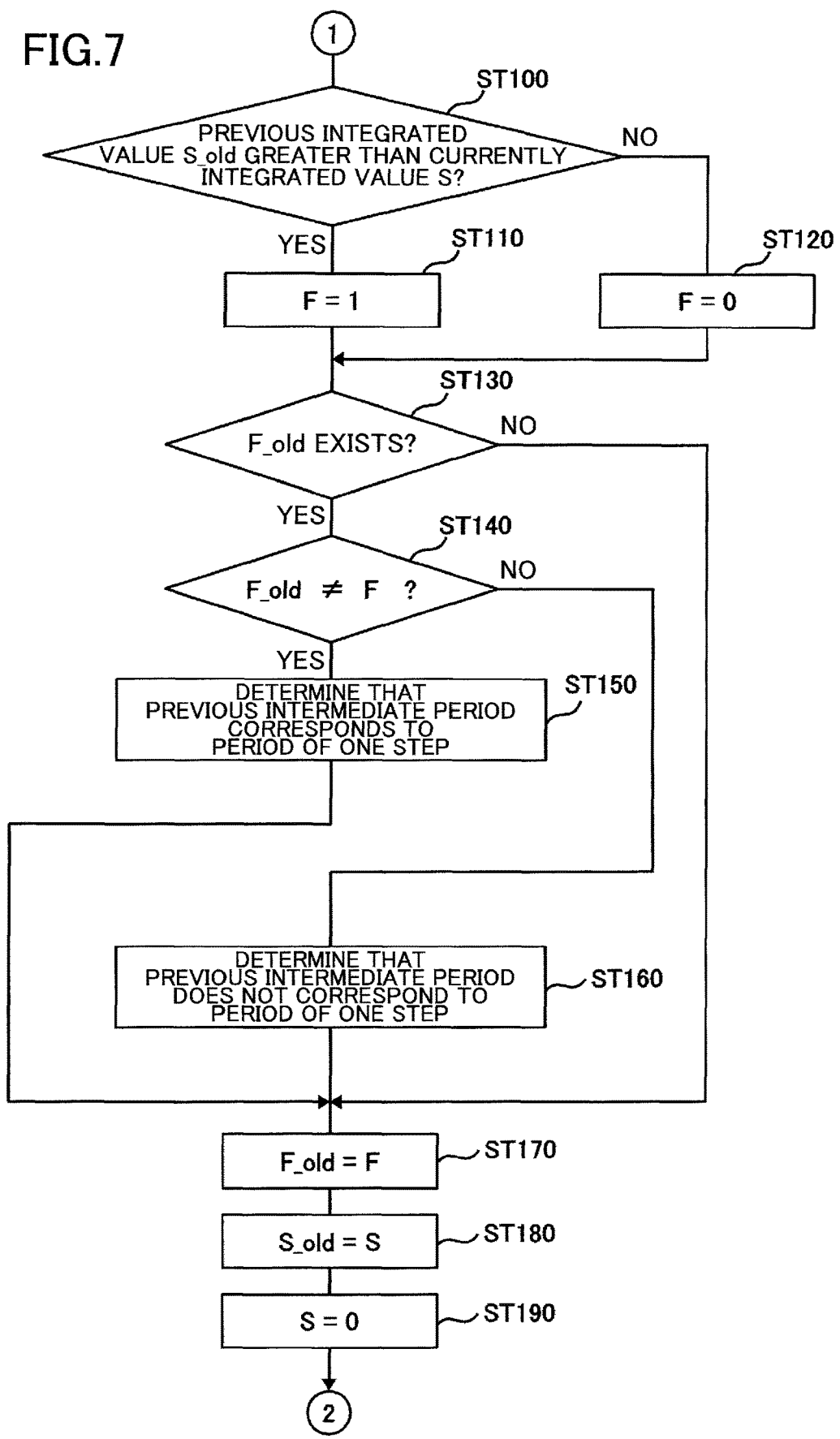
FIG. 7 is a second flowchart illustrating operations of the walking measurement device according to the first embodiment.

FIGS. 6 and 7 are flowcharts illustrating operations of the walking measurement device 1 according to the present embodiment.

In step ST10, to start measurement operations, the processing unit 20 initializes variables to be used in processes (e.g., integrated values S and S_old, comparison determination values F and F_old).

In step ST20, the processing unit 20 determines whether it is currently the acceleration detection timing, which is set to repeatedly occur at predetermined time intervals. When it is currently the detection timing, the processing unit 20 proceeds to step ST30.

In step ST30, the processing unit 20 acquires the lateral acceleration Ax, the anterior-posterior acceleration Ay, and the vertical acceleration Az detected by the acceleration sensor 10.

In step ST40, based on the accelerations Ax, Ay, and Az acquired in step ST30, the timing detection unit 21 calculates the evaluation value E using the above formula (1).

In step ST50, the timing detection unit 21 performs a peak detection process for detecting the timing of a peak occurrence in which the peak of the evaluation value E exceeds the threshold Eth.

For example, when the evaluation value E exceeds the threshold value Eth, the timing detection unit 21 monitors the maximum value Emax of the evaluation value E and stores the maximum value Emax in the storage unit 30. More specifically, each time a new evaluation value E is calculated in step ST40, the timing detection unit 21 compares the new evaluation value E with the maximum value Emax stored in the storage unit 30. When the new evaluation value E exceeds the maximum value Emax, the timing detection unit 21 stores the new evaluation value E in the storage unit 30 as the maximum value Emax. When the new evaluation value E falls below a predetermined threshold value $\Delta E$ as compared with the maximum value Emax, the timing detection unit 21 detects the timing at which this maximum value Emax was obtained as the impact generation timing.

Note that in some embodiments, the timing detection unit 21 may monitor the maximum value Emax of the evaluation value E over a period from when the evaluation value E exceeds the threshold value Eth until the evaluation value E falls below the threshold value Eth and detect the timing at which this maximum value Emax was obtained as the impact generation timing.

In step ST60, the processing unit 20 determines whether a peak of the evaluation value E has been detected. If a peak has been detected, the processing unit 20 proceeds to step ST100 of FIG. 7, and if a peak has not yet been detected, the processing unit 20 proceeds to step ST70.

In step ST70, the acceleration integration unit 22 adds the lateral acceleration Ax acquired in step ST30 to the integrated value S.

In steps ST80, the processing unit 20 determines whether it is currently the acceleration detection timing, which is set to repeatedly occur at predetermined time intervals. When it is currently the acceleration detection timing (YES in step ST80), the processing unit 20 returns to step ST30 and repeats the same process operations as described above. In step ST90, the processing unit 20 determines whether a command instructing the termination of the measurement operations has been input from the communication unit 40, for example. If such a termination command has been input (YES in step ST90), the processing unit 20 ends the measurement operations.

In step ST100, when a peak of the evaluation value E has been detected by the timing detection unit 21, the first determination unit 24 compares a current integrated value S calculated by the acceleration integration unit 22 for the most recent (current) intermediate period T(n) with a previous integrated value S_old calculated for the previous intermediate period T(n−1). When the previous integrated value S_old is greater than the current integrated value S, the first determination unit 24 sets the current comparison determination value F to "1" (step ST110), and if the previous integrated value S_old is not greater than the current integrated value S, the first determination unit 24 sets the current comparison determination value F to "0" (step ST120).

In step ST130, the second determination unit 25 determines whether a previous comparison determination value F_old exists. For example, because the comparison determination value F_old is set to an initial value other than "0" or "1" in step ST10, when the comparison determination value F_old is not equal to "0" or "1", the second determination unit 25 may determine that a previous comparison determination value F_old does not exist. If a previous comparison determination value F_old does exist, the second determination unit 25 proceeds to step ST140. On the other hand, if a previous comparison determination value F_old does not exist, the second determination unit 25 proceeds to step ST180.

In step ST140, the second determination unit 25 determines whether the previous comparison determination value F_old is different from the current comparison determination value F. If the previous comparison determination value F_old is different from the current comparison determination value F, the second determination unit 25 determines that the previous intermediate period T(n−1) corresponds to the period of one step of the walking motion (step ST150) and proceeds to step ST170. On the other hand, if the previous comparison determination value F_old and the current comparison determination value F are the same, the second determination unit 25 determines that the previous intermediate period T(n−1) does not correspond to the period of one step of the walking motion (step ST160), and proceeds to step ST170.

In steps ST170 to ST190, the processing unit 20 initializes the variables in preparation for the next process loop. That is, the processing unit 20 substitutes the comparison determination value F for the comparison determination value F_old (step ST170). Further, the processing unit 20 substitutes the integrated value S for the integrated value S_old (step ST180), and initializes the integrated value S to zero (step ST190). After initializing the variables, the processing unit 20 returns to step ST80 and waits for the next acceleration detection timing.

As described above, according to an aspect of the present embodiment relating to the walking measurement device 1, when a normal walking motion is performed, the rightward acceleration Ax becomes dominant in the left foot landing period, and the leftward acceleration Ax becomes dominant in the right foot landing period. Accordingly, an integrated value S of the acceleration Ax over an intermediate period between two consecutive impact generation timings changes in a regular pattern by alternately increasing and decreasing with respect to each step. Thus, by comparing the integrated values S of the acceleration Ax over two consecutive intermediate periods that are temporally separated by one impact generation timing, it is possible to determine whether the one impact generation timing corresponds to the landing timing of the left foot or the landing timing of the right foot. In this way, more detailed information on the walking motion can be obtained as compared with a conventional pedometer that simply counts the number times an impact has been generated from a foot landing.

Also, according to another aspect of the present invention relating to the walking measurement device 1, by referring to the regular pattern of changes occurring in the lateral acceleration Ax as well as the impact generation timing of the impact generated by the landing of the foot, the period of one step of a walking motion can be accurately determined. For example, when an irregular pattern of change in the integrated value S occurs, such as the integrated values S14 to S18 in FIG. 5, the intermediate periods corresponding to these integrated values are not determined to correspond to the period of one step of the walking motion. Thus, even when the acceleration sensor 10 detects an acceleration unrelated to the walking motion, the walking measurement device 1 may be less likely to erroneously determine such irrelevant acceleration as that resulting from a walking motion.

According to another aspect of the present embodiment relating to the walking measurement device 1, the impact generation timing of the impact generated by the landing of the foot is detected based on the accelerations in the plurality of directions detected by the acceleration sensor 10, and in this way, the configuration of the walking measurement device 1 can be simplified as compared with a device that uses a dedicated sensor to measure the impact.

Second Embodiment

In the following, a second embodiment of the present invention will be described.

Figure 8:
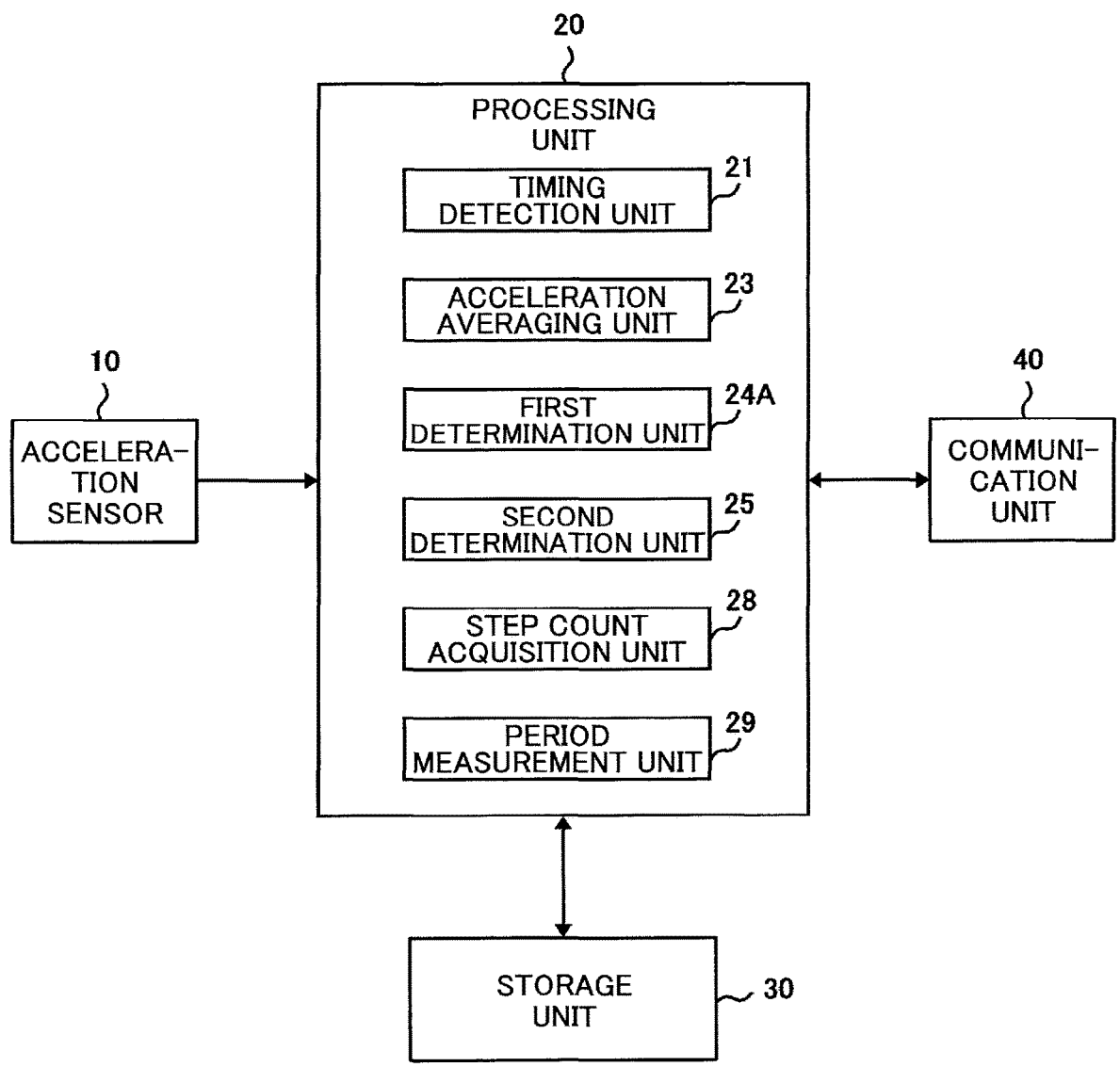
FIG. 8 is a diagram showing an example configuration of a walking measurement device according to a second embodiment of the present invention.

FIG. 8 is a diagram showing an example configuration of a walking measurement device 1A according to the second embodiment. The walking measurement deice 1A shown in FIG. 8 differs from the walking measurement device 1 shown in FIG. 1 in that the acceleration integration unit 22 in the processing unit 20 is replaced by an acceleration averaging unit 23, and the first determination unit 24 is replaced by a first determination unit 24A. Note that other features of the walking measurement device 1A of FIG. 8 may be substantially identical to those of the walking measurement device 1 shown in FIG. 1.

The acceleration averaging unit 23 obtains an average value (average acceleration) of the lateral acceleration detected by the acceleration sensor 10. For example, the acceleration averaging unit 23 may calculate a moving average of the lateral acceleration over a time period in which the timing detection unit 21 detects a predetermined number of impact generation timings.

The first determination unit 24A compares the lateral acceleration detected by the acceleration sensor 10 at one impact generation timing with a threshold value, and based on the comparison result, determines whether the impact generation timing corresponds to the landing timing of the left foot or the landing timing of the right foot.

As shown in FIGS. 4 and 5, the leftward acceleration is relatively high when the left foot lands on the ground, and the rightward acceleration is relatively high when the right foot lands on the ground. Thus, by comparing a lateral acceleration detected by the acceleration sensor 10 at one impact generation timing with an appropriate threshold value, it can be determined whether the impact generation timing corresponds to the landing timing of the right foot or the landing timing of the left foot.

The first determination unit 24A uses the average acceleration of the lateral acceleration calculated by the acceleration averaging unit 23 as the threshold value for making the above determination. In this way, even when there is an imbalance between the leftward acceleration and the rightward acceleration due to an inclined posture, for example, an accurate determination can still be made as to whether a foot landing corresponds to a left foot landing or a right foot landing.

Figure 9:
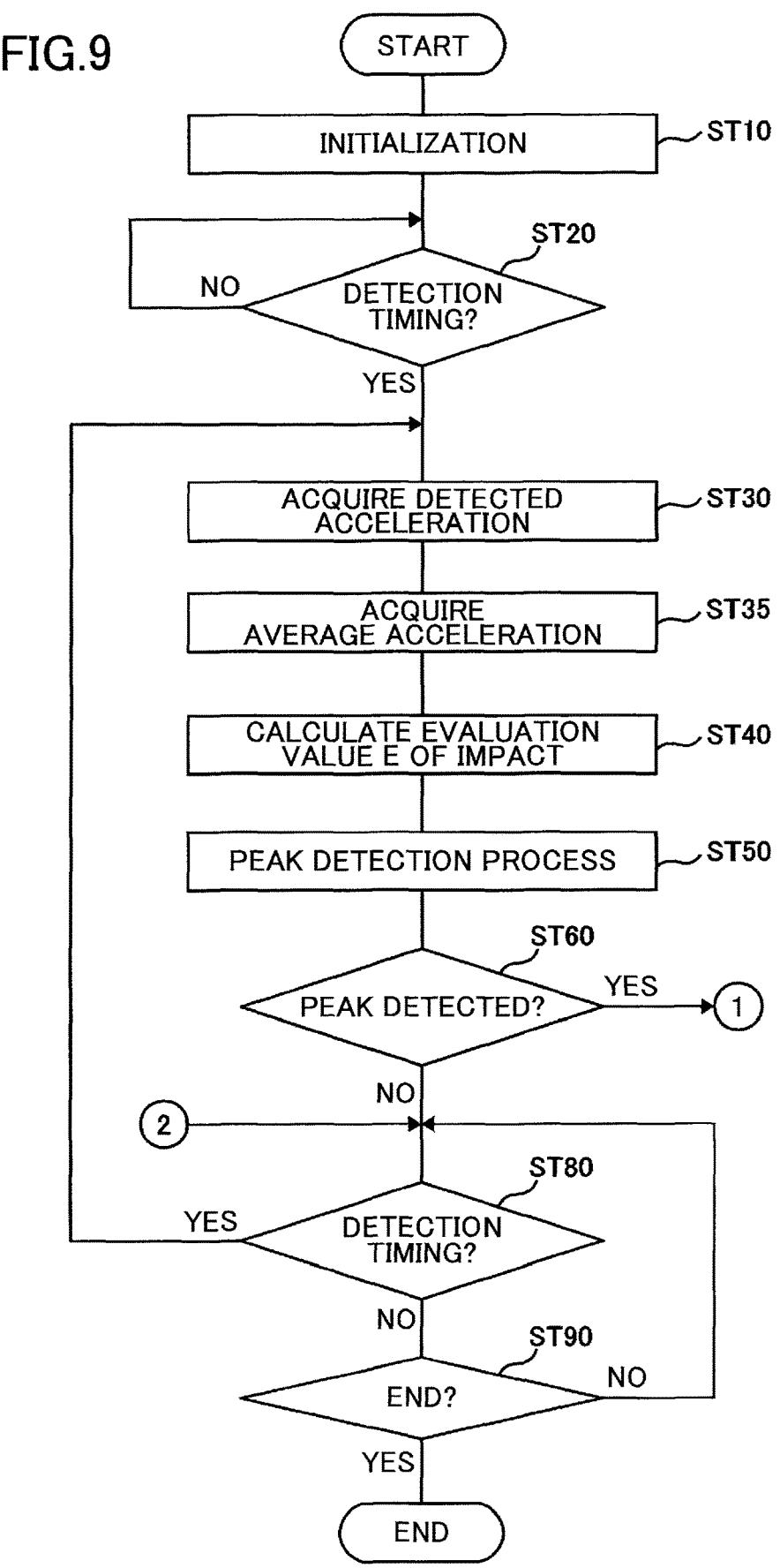
FIG. 9 is a first flowchart illustrating operations of the walking measurement device according to the second embodiment.
Figure 10:
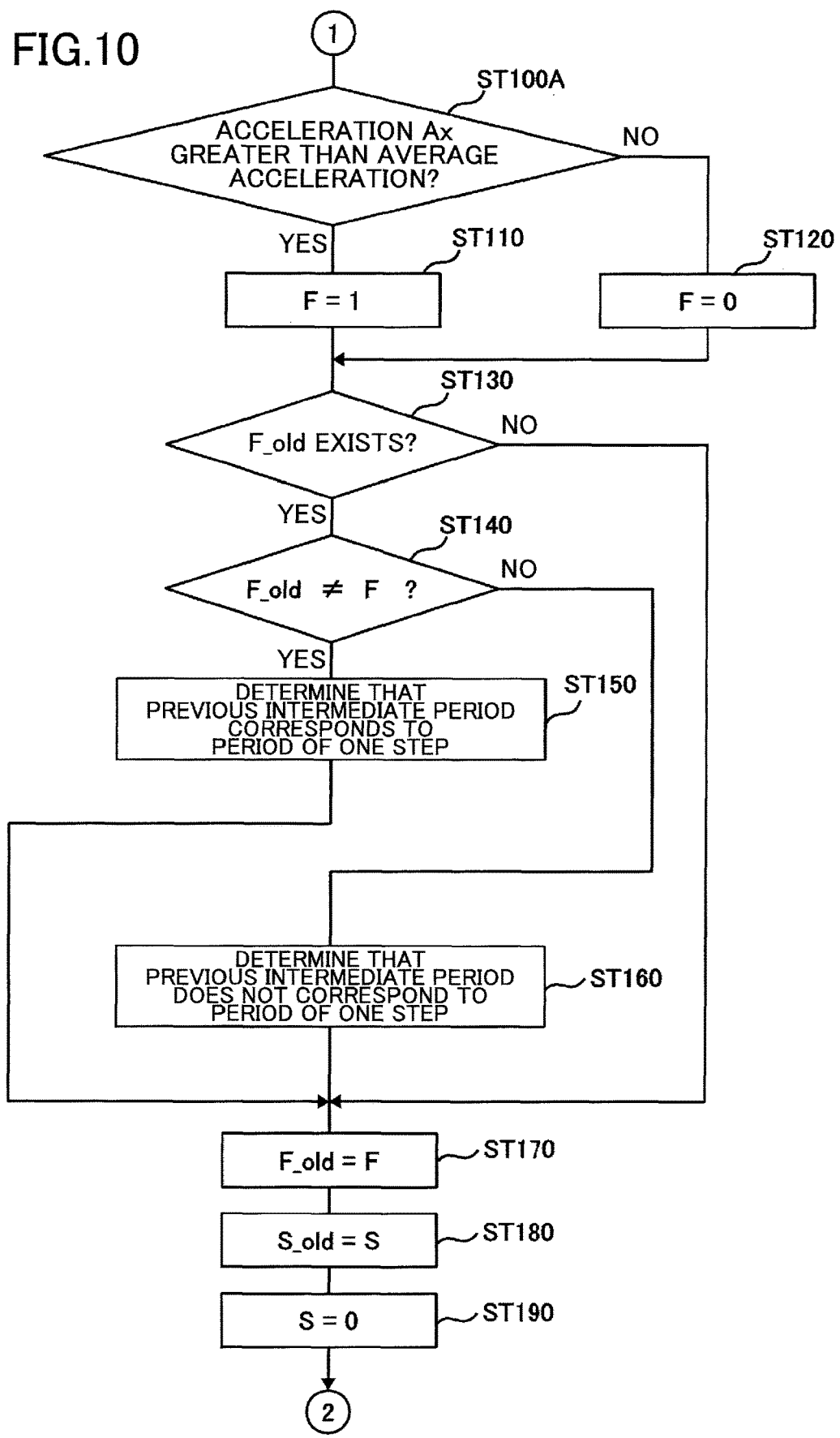
FIG. 10 is a second flowchart illustrating operations of the walking measurement device according to the second embodiment.

FIGS. 9 and 10 are flowcharts illustrating operations of the walking measurement device 1A according to the present embodiment. In FIGS. 9 and 10, step ST70 of FIG. 6 is omitted, step ST35 is added as an additional step in FIG. 9, and step ST100 of FIG. 7 is replaced by step ST100A in FIG. 10. Note that other process steps of FIGS. 9 and 10 may be substantially identical to those of FIGS. 6 and 7.

In the following, only the process steps of FIGS. 9 and 10 that have been added or changed from those of FIGS. 6 and 7 will be described.

Each time the acceleration is detected by the acceleration sensor 10 in step ST30, the acceleration averaging unit 23 calculates an average value of the lateral acceleration (average acceleration) using the acceleration newly detected in step ST30 (step ST35).

When a peak of the evaluation value E is detected by the timing detection unit 21, the first determination unit 24A compares the lateral acceleration Ax detected at the peak detection timing with the average acceleration calculated in step ST35 (step ST100A). When the lateral acceleration Ax is greater than the average acceleration, the first determination unit 24A sets the current comparison determination value F to "1" (step ST110), and if the lateral acceleration Ax is not greater than the average acceleration, the first determination unit 24A sets the current comparison determination value F to "0" (step ST120).

The above-described walking measurement device 1A according to the present embodiment can achieve advantageous effects similar to those achieved by the walking measurement device 1 according to the first embodiment.

Third Embodiment

In the following, a third embodiment of the present invention will be described.

Figure 11:
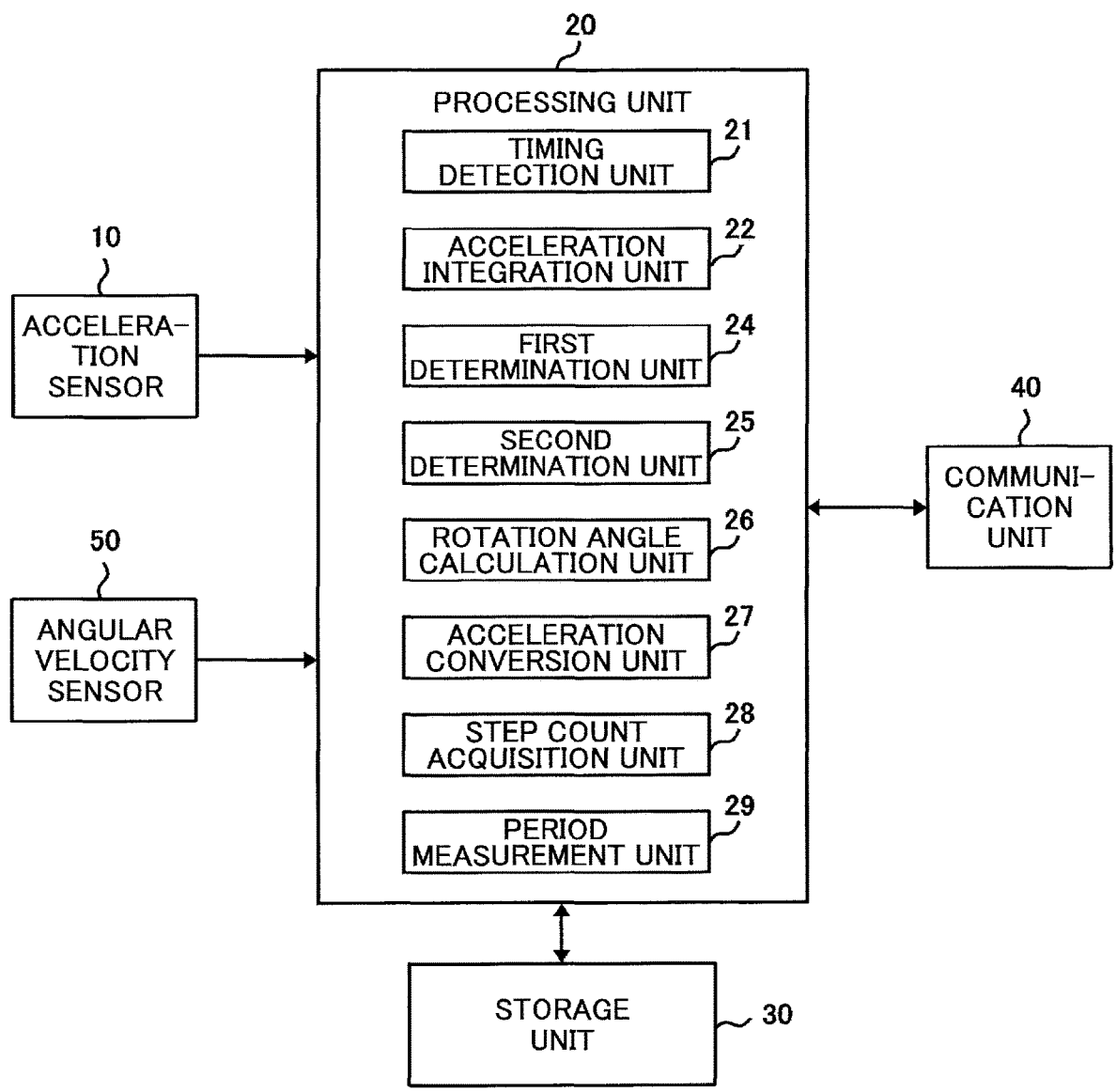
FIG. 11 is a diagram showing an example configuration of a walking measurement device according to a third embodiment of the present invention.

FIG. 11 is a diagram showing an example configuration of a walking measurement device 1B according to the third embodiment. In the walking measurement device 1B shown in FIG. 11, an angular velocity sensor 50 is added as an additional element to the walking measurement device 1 shown in FIG. 1, and a rotation angle calculation unit 26 and an acceleration conversion unit 27 are added as additional elements of the processing unit 20. Note that other features of the walking measurement device 1B shown in FIG. 11 may be substantially identical to those of the walking measurement device 1 shown in FIG. 1.

The angular velocity sensor 50 detects angular velocities along the three axes corresponding to the three directions of the accelerations detected by the acceleration sensor 10 (X-axis direction, Y-axis direction, Z-axis direction in FIGS. 2 and 3).

The rotation angle calculation unit 26 calculates rotation angles around the three axes based on the angular velocities along the three axes detected by the angular velocity sensor 50. For example, the rotation angle calculation unit 26 may calculate the rotation angle around each axis by integrating the angular velocity along the corresponding axis that is detected at periodic intervals by the angular velocity sensor 50.

The acceleration conversion unit 27 uses the rotation angles around the three axes calculated by the rotation angle calculation unit 26 that correspond to rotation angles with respect to a reference posture, which is based on the direction of gravity (described below with reference to FIG. 12A), to convert the three accelerations (Ax, Ay, Az) that are repeatedly detected at certain time intervals by the acceleration sensor 10 into corresponding accelerations with respect to the reference posture (Ax', Ay', Az').

FIGS. 12A-12C are diagrams describing an acceleration conversion process for converting accelerations according to a posture change. FIG. 12A illustrates an example reference posture. The reference posture may be an upright posture with the neck oriented in the vertical direction as shown in FIG. 12A, for example. FIGS. 12B and 12C illustrate an example inclined posture that is inclined with respect to the reference posture.

As shown in FIG. 12B and FIG. 12C, when a posture changes with respect to the reference posture, the three directions (X-axis, Y-axis, Z-axis) corresponding to acceleration detection directions of the acceleration sensor 10 are inclined toward the direction of gravity. Thus, even with the same acceleration, the acceleration detected in an inclined posture is different from the acceleration detected in the reference posture. In order to correctly detect the leftward and rightward accelerations generated in a walking motion, a lateral acceleration with respect to the reference posture (acceleration in the direction horizontal to the ground) has to be obtained. However, the lateral acceleration Ax in the X-axis direction detected by the acceleration sensor 10 in an inclined posture will be different from the lateral acceleration that would be detected in the reference posture.

In this respect, the walking measurement device 1B according to the present embodiment uses the angular velocities detected by the angular velocity sensor 50 to perform an acceleration conversion process for converting accelerations detected in an inclined posture (Ax, Ay, Az) into corresponding accelerations with respect to the reference posture (Ax', Ay', Az').

When a posture changes with respect to the reference posture, rotations occur around the three axes corresponding to the angular velocity detection axes of the angular velocity sensor 50 according to the inclinations of the three axes with respect to the reference posture. Thus, the rotation angles of the three axes with respect to the reference posture (FIG. 12A) that are calculated by the rotation angle calculation unit 26 represent the inclinations of the detection directions (X-axis, Y-axis, Z-axis) of the acceleration sensor 10 with respect to the reference posture. The acceleration conversion unit 27 converts the accelerations in the three directions (Ax, Ay, Az) detected in an inclined posture that is inclined with respect to the reference posture into corresponding accelerations with respect to the reference posture (Ax', Ay', Az'), based on the rotation angles of the three axes with respect to the reference posture.

According to an aspect of the present embodiment relating to the walking measurement device 1B, even when the acceleration detection directions (X-axis, Y-axis, Z-axis) of the acceleration sensor 10 are inclined with respect to the reference posture as a result of a change in posture with respect to the reference posture, corresponding accelerations with respect to the reference posture can be accurately obtained.

Note that in some embodiments, the acceleration conversion unit 27 may be configured to convert only the lateral acceleration (Ax), or may be configured to convert the accelerations in the other directions (Ay, Az) as needed, for example.

Although the present invention has been described above with respect to certain illustrative embodiments, the present invention is not limited to the above-described embodiments. That is, those skilled in the art may make various changes, modifications, and substitutions for the above-described embodiments without departing from the scope of the present invention.

In the above-described embodiments, an impact generated by the landing of the left foot or the right foot is detected based on accelerations in a plurality of directions detected by the acceleration sensor 10. However, the present invention is not limited to these embodiments. For example, in some embodiments of the present invention, the impact associated with the a foot landing may be detected by a sensor other than the acceleration sensor 10. For example, the impact of a foot landing may be determined based on detections made by an acceleration sensor attached at the waist or the foot, a pressure sensor attached at the back of the heel, and the like.

Although the walking motion of a human is subject to measurement in the above-described embodiments, the present invention is not limited to these embodiments. In some embodiments of the present invention, the walking motion of an animal, a machine, or some object other than a human may be subject to measurement.

In the following, further aspects and embodiments of the present invention are described.

According to a first aspect of the present invention, a walking measurement device is provided that includes a timing detection unit that detects an impact generation timing at which an impact resulting from a landing of a left foot or a right foot has been generated; an acceleration sensor that repeatedly detects, at predetermined time intervals, an acceleration in a lateral direction along which the left foot and the right foot are arranged side by side; and a first determination unit that determines whether the impact generation timing corresponds to a landing timing of the left foot or a landing timing of the right foot based on the impact generation timing detected by the timing detection unit and the acceleration detected by the acceleration sensor.

With the above-described configuration, it is possible to determine whether the left foot or the right foot has landed at the time an impact of a foot landing has been generated based on the detected impact generation timing and the acceleration in the lateral direction along which the left foot and the right foot are arranged side by side.

In one example embodiment, the above-described walking measurement device may further include an acceleration integration unit that acquires an integrated value of the acceleration in the lateral direction detected by the acceleration sensor over an intermediate period between two consecutive impact generation timings consecutively detected by the timing detection unit. The first determination unit may compare two integrated values acquired with respect to two consecutive intermediate periods that are temporally separated by one impact generation timing and determine whether the one impact generation timing corresponds to the landing timing of the left foot or the landing timing of the right foot based on the result of the comparison.

During the period from when the left foot lands on the ground until the right foot lands on the ground (hereinafter referred to as "left foot landing period"), the acceleration in the direction from the left side to the right side (hereinafter referred to as "rightward acceleration") becomes more dominant as compared with the acceleration in the direction from the right side to the left side (hereinafter referred to as "leftward acceleration"). On the other hand, during the period from when the right foot lands on the ground until the left foot lands on the ground (hereinafter referred to as "right foot landing period"), the leftward acceleration becomes more dominant as compared with the rightward acceleration. Assuming the rightward acceleration detected by the acceleration sensor is greater than the leftward acceleration detected by the acceleration sensor, the integrated value of the acceleration over the left landing period in which the rightward acceleration becomes dominant will be greater than the integrated value of the acceleration over the right foot landing period in which the leftward acceleration becomes dominant. That is, the integrated value for the left foot landing period and the integrated value for the right foot landing period have a fixed magnitude correlation. Thus, by comparing the integrated values acquired with respect to two consecutive intermediate periods that are temporally separated by one impact generation timing, it is possible to determine whether the one impact generation timing corresponds to the landing timing of the left foot or the landing timing of the right foot.

Also, in one example embodiment, the first determination unit may compare the acceleration in the lateral direction detected by the acceleration sensor at one impact generation timing with a threshold value and determine whether the one impact generation timing corresponds to the landing timing of the left foot or the landing timing of the right foot based on the result of the comparison.

The leftward acceleration is relatively high when the left foot lands on the ground, and the rightward acceleration is relatively high when the right foot lands on the ground. Thus, by comparing the acceleration detected by the acceleration sensor at one impact generation timing with a threshold value, it is possible to determine whether the one impact generation timing corresponds to the landing timing of the left foot or the landing timing of the right foot.

Also, in one example embodiment, the above-described walking measurement device may further include an acceleration averaging unit that obtains an average value of the acceleration in the lateral direction detected by the acceleration sensor. The first determination unit may compare the acceleration in the lateral direction detected by the acceleration sensor at one impact generation timing with the average value obtained at a proximate time to the one impact generation timing and determine whether the one impact generation timing corresponds to the landing timing of the left foot or the landing timing of the right foot based on the result of the comparison.

In this way, the determination of whether the one impact generation timing corresponds to the landing timing of the left foot or the landing timing of the right foot can be accurately made even when there is an imbalance between the leftward acceleration and the rightward acceleration due to an inclined posture, for example.

Also, in one example embodiment, the above-described walking measurement device may further include a second determination unit that determines whether an intermediate period between two consecutive impact generation timings corresponds to a period of one step of a walking motion. When two determination results obtained by the first determination unit with respect to the two consecutive impact generation timings are different from each other, the second determination unit may determine that one intermediate period, from among three consecutive intermediate periods that are temporally separated by the two consecutive impact generation timings, corresponds to the period of one step of the walking motion.

Because a normal walking motion involves alternating between landing with the left foot and landing with the right foot, the left/right determination of the foot landing made by the first determination unit should alternate between left and right with respect to each step. Thus, when two determination results obtained by the first determination unit with respect to two consecutive impact generation timings are different from each other, the second determination unit may determine that one intermediate period, from among three consecutive intermediate periods that are temporally separated by the two consecutive impact generation timings, corresponds to the period of one step of the walking motion. By referring to the left/right determination result of a foot landing at a given impact generation timing in addition to the impact generation timing at which the impact of the foot landing has been generated as described above, the period of one step of the walking motion can be more accurately determined.

Also, in one example embodiment, the acceleration sensor may detect a positive acceleration when the acceleration is in one direction in the lateral direction, and the acceleration sensor may detect a negative acceleration when the acceleration is in an opposite direction of the one direction in the lateral direction.

Also, in one example embodiment, the acceleration sensor may repeatedly detect a plurality of accelerations in a plurality of different directions, including the lateral direction, at the predetermined time intervals. The timing detection unit may detect the impact generation timing at which the impact has been generated based on the plurality of accelerations in the plurality of directions detected by the acceleration sensor.

With the above-described configuration, the walking measurement device can detect the impact generation timing at which an impact of a foot landing has been generated based on the accelerations detected by the acceleration sensor such that a dedicated sensor would not be required and the device configuration can be simplified.

Also, in one example embodiment, the timing detection unit may calculate an evaluation value indicating a magnitude of the impact based on the plurality of accelerations in the plurality of directions detected by the acceleration sensor and detect, as the impact generation timing, a timing at which a peak of the evaluation value that exceeds a predetermined threshold value has occurred.

In a normal walking motion, an impact resulting from a foot landing is comparatively greater than an impact cause by other factors. As such, by detecting the impact generation timing of the impact resulting from the landing of the foot based on the timing at which a peak exceeding a predetermined threshold value occurs in the evaluation values as described above, the impact generation timing can be appropriately detected.

Also, in one example embodiment, the timing detection unit may calculate the evaluation value based on a sum of the squared values of the plurality of accelerations in the plurality of directions detected by the acceleration sensor.

With the above-described configuration, when the absolute values of the accelerations in the plurality of directions increase as a result of the impact generated from a foot landing, the evaluation values increase accordingly.

Also, in one example embodiment, the acceleration sensor may detect at least one of an acceleration in a vertical direction and an acceleration in an anterior-posterior direction that is perpendicular to the lateral direction and the vertical direction.

Also, in one example embodiment, the acceleration sensor may detect three accelerations in three directions, including the lateral direction, that are substantially perpendicular to each other. The walking measurement device may further include an angular velocity sensor that detects angular velocities around three axes corresponding to the three directions of the three accelerations detected by the acceleration sensor; a rotation angle calculation unit that calculates rotation angles around the three axes based on the angular velocities around the three axes detected by the angular velocity sensor; and an acceleration conversion unit that converts at least the acceleration in the lateral direction, from among the three accelerations repeatedly detected by the acceleration sensor at the predetermined time intervals, into a corresponding acceleration with respect to a reference posture, based on the rotation angles around the three axes calculated by the rotation angle calculation unit that correspond to rotation angles with respect to the reference posture, which is based on a direction of gravity.

When a posture changes with respect to the reference posture, which is based on the direction of gravity, the three directions corresponding to the acceleration detection directions of the acceleration sensor will be inclined with respect to the direction of gravity. In such case, rotations according to the inclinations of the three directions occur around the three axes corresponding to the angular velocity detection axes of the angular velocity sensor. The rotation angles around the three axes with respect to the reference posture that are calculated by the rotation angle calculation unit represent the inclinations of the detection directions of the acceleration sensor with respect to the reference posture. The acceleration conversion unit converts at least the acceleration in the lateral direction, from among the accelerations in the three directions detected in the inclined posture with respect to the reference posture, into a corresponding acceleration with respect to the reference posture, based on the rotation angles around the three axes with respect to the reference posture. Thus, even when the acceleration detection directions of the acceleration sensor are inclined with respect to the acceleration detection directions in the reference posture due to a posture change with respect to the reference posture, at least the acceleration in the lateral direction with respect to the reference posture can be accurately detected.

Also, in one example embodiment, the acceleration sensor may be mounted at the head.

In this way, desired detection sensitivity for detecting the acceleration in the lateral direction associated with a walking motion may be achieved.

Also, in one example embodiment, the above-described walking measurement device may further include a step count acquisition unit that counts a number of times a second determination unit has determined that the intermediate period corresponds to a period of one step of a walking motion and acquire the counted number as a number of steps.

In this way, an accurate number of steps can be acquired.

According to a second aspect of the present invention, a walking measurement method is provided that is implemented by a computer to measure a walking motion based on a detection result of an acceleration sensor that detects an acceleration in a lateral direction along which a left foot and a right foot are arranged side by side. The walking measurement method includes steps of detecting an impact generation timing at which an impact resulting from a landing of the left foot or the right foot has been generated; controlling the acceleration sensor to repeatedly detect the acceleration in the lateral direction at predetermined time intervals; and determining, based on the detected impact generation timing and the detected acceleration, whether the impact generation timing corresponds to a landing timing of the left foot or a landing timing of the right foot.

In one example embodiment, the above-described walking measurement method may further include steps of acquiring an integrated value of the acceleration in the lateral direction detected by the acceleration sensor over an intermediate period between two consecutive impact generation timings that have been consecutively detected; and comparing two integrated values acquired with respect to two consecutive intermediate periods that are temporally separated by one impact generation timing and determining whether the one impact generation timing corresponds to the landing timing of the left foot or the landing timing of the right foot based on a result of the comparison.

Also, in one example embodiment, the above-described walking measurement method may further include steps of comparing the acceleration in the lateral direction detected by the acceleration sensor at one impact generation timing with a threshold value, and determining whether the one impact generation timing corresponds to the landing timing of the left foot or the landing timing of the right foot based on a result of the comparison.

Also, in one example embodiment, the above-described walking measurement method may further include steps of obtaining an average value of the acceleration in the lateral direction detected by the acceleration sensor, comparing the acceleration in the lateral direction detected by the acceleration sensor at one impact generation timing with the average value obtained at a proximate time to the one impact generation timing, and determining whether the one impact generation timing corresponds to the landing timing of the left foot or the landing timing of the right foot based on a result of the comparison.

Also, in one example embodiment, the above-described walking measurement method may further include steps of determining whether an intermediate period between two consecutive impact generation timings corresponds to a period of one step of a walking motion; and upon determining that results of determining whether the two consecutive impact generation timings correspond to the landing timing of the left foot or the landing timing of the right foot are different from each other, determining that one intermediate period, from among three intermediate time periods that are temporally separated by the two consecutive impact generation timings, corresponds to the period of one step.

Also, in one example embodiment, the acceleration sensor may be controlled to detect a plurality of accelerations in a plurality of different directions, including the lateral direction, at the predetermined time intervals. The impact generation timing may be detected based on the plurality of accelerations in the plurality of directions detected by the acceleration sensor.

Also, in one example embodiment, the above-described walking measurement method may further include steps of controlling the acceleration sensor to detect three accelerations in three directions, including the lateral direction, that are substantially perpendicular to each other; controlling an angular velocity sensor to detect angular velocities around three axes corresponding to the three directions of the three accelerations detected by the acceleration sensor; calculating rotation angles around the three axes based on the angular velocities around the three axes detected by the angular velocity sensor; and converting at least the acceleration in the lateral direction, from among the three accelerations repeatedly detected by the acceleration sensor at the predetermined time intervals, into a corresponding acceleration with respect to a reference posture, based on the calculated rotation angles around the three axes that correspond to rotation angles with respect to the reference posture, which is based on a direction of gravity.

According to a third aspect of the present invention, a program is provided that causes a computer to execute the above-described walking measurement method according to the second aspect of the present invention.

What is claimed is:

1. A walking measurement device, comprising:
a timing detection circuit configured to detect an impact generation timing at which an impact resulting from a landing of a left foot or a right foot has been generated;
an acceleration sensor configured to repeatedly detect, at predetermined time intervals, an acceleration in a lateral direction along which the left foot and the right foot are arranged side by side;
a first determination circuit configured to determine whether the impact generation timing corresponds to a landing timing of the left foot or a landing timing of the right foot based on the impact generation timing detected by the timing detection circuit and the acceleration detected by the acceleration sensor; and
an acceleration integration circuit configured to acquire an integrated value of the acceleration in the lateral direction detected by the acceleration sensor over an intermediate period between two consecutive impact generation timings consecutively detected by the timing detection circuit,
wherein the first determination circuit compares two integrated values acquired with respect to two consecutive intermediate periods that are temporally separated by one impact generation timing and determines whether the one impact generation timing corresponds to the landing timing of the left foot or the landing timing of the right foot based on a result of the comparison,
the walking measurement device further comprising:
a second determination circuit configured to determine whether an intermediate period between two consecutive impact generation timings corresponds to a period of one step of a walking motion,
wherein when two determination results obtained the first determination circuit with respect to the two consecutive impact generation timings are different from each other, the second determination circuit determines that an intermediate period between the two consecutive impact generation timings corresponds to the period of one step, and
wherein when the two determination results obtained by the first determination circuit with respect to the two consecutive impact generation timings are the same, the second determination circuit determines that the intermediate period between the two consecutive impact generation timings does not correspond to the period of one step.

2. The walking measurement device according to claim 1, wherein
the first determination circuit compares the acceleration in the lateral direction detected by the acceleration sensor at one impact generation timing with a threshold value and determines whether the one impact generation timing corresponds to the landing timing of the left foot or the landing timing of the right foot based on a result of the comparison.

3. The walking measurement device according to claim 2, farther comprising:
an acceleration averaging circuit configured to obtain an average value of the acceleration in the lateral direction detected by the acceleration sensor;
wherein the first determination circuit compares the acceleration in the lateral direction detected by the acceleration sensor at one impact generation timing with the average value obtained at a proximate time to the one impact generation timing and determines whether the one impact generation timing corresponds to the landing timing of the left foot or the landing timing of the right foot based on a result of the comparison.

4. The walking measurement device according to claim 1, wherein
the acceleration sensor detects a positive acceleration when the acceleration is in one direction in the lateral direction, and the acceleration sensor detects a negative acceleration when the acceleration is in an opposite direction of the one direction in the lateral direction.

5. The walking measurement device according to claim 1, wherein
the acceleration sensor repeatedly detects a plurality of accelerations in a plurality of different directions, including the lateral direction, at the predetermined time intervals; and
the timing detection circuit detects the impact generation timing at which the impact has been generated based on the plurality of accelerations in the plurality of directions detected by the acceleration sensor.

6. The walking measurement device according to claim 5, wherein
the timing detection circuit calculates an evaluation value indicating a magnitude of the impact based on the plurality of accelerations in the plurality of directions detected by the acceleration sensor and detects, as the impact generation timing, a timing; at which a peak of the evaluation value that exceeds a predetermined threshold value has occurred.

7. The walking measurement device according to claim 6, wherein
the timing detection circuit calculates the evaluation value based on a sum of the squared values of the plurality of accelerations in the plurality of directions detected by the acceleration sensor.

8. The walking measurement device according to claim 5, wherein
the acceleration sensor detects at least one of an acceleration in a vertical direction and an acceleration in an anterior-posterior direction that is perpendicular to the lateral direction and the vertical direction.

9. The walking measurement device according to claim 1, wherein
the acceleration sensor detects three accelerations in three directions, including the lateral direction, that are perpendicular to each other,
the walking measurement device further comprising:
an angular velocity sensor configured to detect angular velocities around three axes corresponding to the three directions of the three accelerations detected by the acceleration sensor;
a rotation angle calculation circuit configured to calculate rotation angles around the three axes based on the angular velocities around the three axes detected by the angular velocity sensor; and
an acceleration conversion circuit configured to convert at least the acceleration in the lateral direction, from among the three accelerations repeatedly detected by the acceleration sensor at the predetermined time intervals, into a corresponding acceleration with respect to a reference posture, based on the rotation angles around the three axes calculated by the rotation angle calculation circuit that correspond to rotation angles with respect to the reference posture, which is based on a direction of gravity.

10. The walking measurement device according to claim 1, wherein the acceleration sensor is mounted at a head.

11. The walking measurement device according to claim 1, further comprising:
a step count acquisition circuit configured to count a number of times a second determination circuit has determined that an intermediate period between two consecutive impact generation timings corresponds to a period of one step of a walking motion and acquire the counted number as a number of steps.

12. A walking measurement method that is implemented by a computer to measure a walking motion based on a detection result of an acceleration sensor that detects an acceleration in a lateral direction along which a left foot and a right foot are arranged side by side, the walking measurement method comprising:
detecting an impact generation timing at which an impact resulting from a landing of the left foot or the right foot has been generated;
controlling the acceleration sensor to repeatedly detect the acceleration in the lateral direction at predetermined time intervals;
determining, based on the detected impact generation timing and the detected acceleration, whether the impact generation timing corresponds to a landing timing of the left foot or a landing timing of the right foot;
acquiring an integrated value of the acceleration in the lateral direction detected by the acceleration sensor over an intermediate period between two consecutive impact generation timings consecutively detected by the detecting;
comparing two integrated values acquired with respect to two consecutive intermediate periods that are temporally separated by one impact generation timing and determining whether the one impact generation timing corresponds to the landing timing of the left foot or the landing timing of the right foot based on a result of the comparing;
determining whether an intermediate period between two consecutive impact generation timings corresponds to a period of one step of a walking motion;
when two determination results obtained by the first determination circuit with respect to the two consecutive impact generation timings are different from each other, determining that an intermediate period between the two consecutive impact generation timings corresponds to the period of one step; and
when the two determination results obtained by the first determination circuit with respect to the two consecutive impact generation timings are the same, determining that the intermediate period between the two consecutive impact generation timings does not.

13. The walking measurement method according to claim 12, further comprising:
acquiring an integrated value of the acceleration in the lateral direction detected by the acceleration sensor over an intermediate period between two consecutive impact generation timings that have been consecutively detected; and
comparing two integrated values acquired with respect to two consecutive intermediate periods that are temporally separated by one impact generation timing and determining whether the one impact generation timing corresponds to the landing timing the left foot or the landing timing of the right foot based on a result of the comparison.

14. The walking measurement method according to claim 12, further comprising:
   comparing the acceleration in the lateral direction detected by the acceleration sensor at one impact generation timing with a threshold value and determining whether the one impact generation timing corresponds to the landing timing of the left foot or the landing timing of the right foot based on a result of the comparison.

15. The walking measurement method according to claim 14, further comprising:
   obtaining an average value of the acceleration in the lateral direction detected by the acceleration sensor; and
   comparing the acceleration in the lateral direction detected by the acceleration sensor at one impact generation timing with the average value obtained at a proximate time to the one impact generation timing and determining whether the one impact generation timing corresponds to the landing timing of the left foot or the landing timing of the right foot based on a result of the comparison.

16. The walking measurement method according to claim 12, further comprising:
   determining whether an intermediate period between two consecutive impact generation timings corresponds to a period of one step of a walking motion; and
   upon determining that results of determining whether the two consecutive impact generation timings correspond to the landing timing of the left foot or the landing timing of the right foot are different from each other, determining that one intermediate period, from among three intermediate time periods that are temporally separated by the two consecutive impact generation timings, corresponds to the period of one step.

17. The walking measurement method according to claim 12, wherein
   the acceleration sensor is controlled to detect a plurality of accelerations in a plurality of different directions, including the lateral direction, at the predetermined time intervals; and
   the impact generation timing is detected based on the plurality of accelerations in the plurality of directions detected by the acceleration sensor.

18. The walking measurement method according to claim 12, further comprising:
   controlling the acceleration sensor to detect three accelerations in three directions, including the lateral direction, that are perpendicular to each other, controlling an angular velocity sensor to detect angular velocities around three axes corresponding to the three directions of the three accelerations detected by the acceleration sensor;
   calculating rotation angles around the three axes based on the angular velocities around the three axes detected b the angular velocity sensor; and
   convening at least the acceleration in the lateral direction, from among the three accelerations repeatedly detected by the acceleration sensor at the predetermined time intervals, into a corresponding acceleration with respect to a reference posture, based on the calculated rotation angles around the three axes that correspond to rotation angles with respect to the reference posture, which is based on a direction of gravity.

19. A non-transitory computer-readable medium storing a computer program that when executed causes a computer to execute the walking measurement method according to claim 12.

* * * * *